United States Patent
Ivanov et al.

(10) Patent No.: US 10,582,901 B2
(45) Date of Patent: Mar. 10, 2020

(54) RECOGNIZER OF STAFF OR PATIENT BODY PARTS USING MARKERS TO PREVENT OR REDUCE UNWANTED IRRADIATION

(71) Applicant: KONINKLIJKE PHILIPS N.V., Eindhoven (NL)

(72) Inventors: Eugene Alekseyevich Ivanov, Eindhoven (NL); Bart Pierre Antoine Jozef Hoornaert, Eindhoven (NL); Raoul Florent, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 130 days.

(21) Appl. No.: 15/303,755

(22) PCT Filed: Apr. 21, 2015

(86) PCT No.: PCT/EP2015/058536
§ 371 (c)(1),
(2) Date: Oct. 13, 2016

(87) PCT Pub. No.: WO2015/162101
PCT Pub. Date: Oct. 29, 2015

(65) Prior Publication Data
US 2017/0215823 A1    Aug. 3, 2017

(30) Foreign Application Priority Data
Apr. 24, 2014    (EP) .................................... 14305600

(51) Int. Cl.
*A61B 6/10*    (2006.01)
*A61B 6/04*    (2006.01)
(Continued)

(52) U.S. Cl.
CPC ............ *A61B 6/107* (2013.01); *A61B 6/0492* (2013.01); *A61B 6/08* (2013.01); *A61B 6/542* (2013.01);
(Continued)

(58) Field of Classification Search
None
See application file for complete search history.

(56) References Cited

U.S. PATENT DOCUMENTS

| 4,103,176 A | 7/1978 | Coyle |
|---|---|---|
| 5,539,798 A | 7/1996 | Asahina |

(Continued)

FOREIGN PATENT DOCUMENTS

| DE | 20017474 U1 | 9/2001 |
|---|---|---|
| DE | 102008045988 A1 | 3/2010 |

(Continued)

OTHER PUBLICATIONS

Chang, Lillian Y. et al "Feature Selection for Grasp Recognition from Optical Markers", IEEE Intelligent Robots and Systems, 2007, pp. 2944-2950.

(Continued)

*Primary Examiner* — Hoon K Song

(57) ABSTRACT

An imaging system and a related method include a marker detection system (MDS) to detect one or more markers (MK) spatially arranged in association with an area (A). If the marker detection system (MDS) detects that the area (A) is within a field-of-view (FoV) of the imaging system or is at least within a predefined distance thereof, a control signal is issued in respect of the area (A) to an image acquisition system (ACS) of the imaging system. The area (A) may be one of a hand of a human operator or a part of a patient to be imaged.

20 Claims, 5 Drawing Sheets

(51) Int. Cl.
    *A61B 6/08* (2006.01)
    *A61B 6/00* (2006.01)
    *A61B 90/00* (2016.01)

(52) U.S. Cl.
    CPC .............. *A61B 6/545* (2013.01); *A61B 90/39* (2016.02); *A61B 2090/3937* (2016.02); *A61B 2090/3966* (2016.02); *A61B 2090/3979* (2016.02)

(56) References Cited

U.S. PATENT DOCUMENTS

| | | |
|---|---|---|
| 6,435,717 B1 | 8/2002 | Kohler |
| 2002/0188194 A1* | 12/2002 | Cosman ............... A61B 6/5247 600/426 |
| 2007/0297572 A1 | 12/2007 | Moritake |
| 2008/0198968 A1 | 8/2008 | Takekoshi |
| 2009/0136000 A1 | 5/2009 | Nishii |
| 2009/0245464 A1* | 10/2009 | Yamaguchi .......... A61B 6/4441 378/62 |
| 2009/0290174 A1 | 11/2009 | Gilboa |
| 2011/0249791 A1 | 10/2011 | Wang |
| 2015/0265179 A1* | 9/2015 | Lonkadi ................. A61B 5/061 600/424 |
| 2015/0363002 A1* | 12/2015 | Fuhrmann .............. A61B 6/465 378/95 |

FOREIGN PATENT DOCUMENTS

| | | |
|---|---|---|
| DE | 102008050572 A1 | 4/2010 |
| EP | 1084678 A1 | 3/2001 |
| JP | 2008125719 A | 6/2008 |
| WO | 200010642 A1 | 3/2000 |
| WO | 2007072356 A2 | 6/2007 |
| WO | 2011047467 A1 | 4/2011 |

OTHER PUBLICATIONS

Bianchi, M. et al "Synergy-based Optimal Design of Hand Pose Sensing", Intelligent Robtos and Systems (IROS), 2012, pp. 3929-3935.

Maeder, Micha et al "Radiation Exposure and Radiation Protection in Interventional Cardiology", Cardiovascular Medicine, vol. 8, 2005, pp. 124-132.

Murthy, Sreerama K. et al "Automatic Collimation in Peripheral X-Ray Imaging", 1998 International Conference IEEE Computer Society.

* cited by examiner

RECOGNIZER OF STAFF OR PATIENT BODY PARTS USING MARKERS TO PREVENT OR REDUCE UNWANTED IRRADIATION

CROSS-REFERENCE TO PRIOR APPLICATIONS

This application is the U.S. National Phase application under 35 U.S.C. § 371 of International Application No. PCT/EB2015/058536, filed on Apr. 21, 2015, which claims the benefit of European Patent Application No. 14305600.0, filed on Apr. 24, 2014. These applications are hereby incorporated by reference herein.

FIELD OF THE INVENTION

The invention relates to an X-ray imaging system, to a method of operating an X-ray imaging system, to at least one marker for encoding one or more image acquisition instructions, to a wearable item including at least one marker encoding one or more image acquisition instructions, to a computer program product and to a computer-readable medium.

BACKGROUND OF THE INVENTION

X-ray imaging forms still one of the main tools in the arsenal of modern medicine for learning clues about the internal structure of a patient. The benefit of being able to look into the patient by using X-rays still needs to be balanced against the dangers of high radiation dosage. For instance, interventional X-ray procedures make ample use of patient imagery. In interventional X-ray procedures, a medical tool (such as catheter) is introduced into the patient whilst the patient is being imaged. One issue is that during interventional X-ray procedures interventionists on occasion place their hands in the direct X-ray beam. This may occur in emergencies, or when clinical task calls. For instance, it has also been observed that some practitioners desire to additionally feel the blood vessels when navigating the equipment, adjust/enforce optimal patient position and etc. Although the dosage incurred by staff through voluntary or involuntary "hand radiation" in this manner may be small for any one intervention in itself, the dosage can quickly accumulate for some staff to worrisome levels over the course of time.

Today the staff "hand irradiation problem" is tackled primarily by education or by encouraging staff to wear lead lined gloves and/or ring dosimeters but these are rarely worn in practice and these measures do not actually prevent irradiation.

One solution is proposed in Applicant's U.S. Pat. No. 6,435,717 where a warning signal is output in the manner of a "motion detector" when, for instance, the interventionist's hand is within a radiation zone. However, this method may prove on occasion unreliable. Another issue with X-ray imaging is unnecessary patient irradiation. Parts of a patient's body sometimes receive dosage in areas unrelated to the region of interest one wishes to image.

SUMMARY OF THE INVENTION

There may therefore be a need in the X-ray imaging art for an alternative system-ray imaging systems with, in particular, more robust or reliable control means.

The object of the present invention is solved by the subject matter of the independent claims where further embodiments are incorporated in the dependent claims. It should be noted that the following described aspect of the invention equally apply to the method of operating an X-ray imaging system, to the computer program element and to the computer readable medium.

According to a first aspect of the invention there is provided an X-ray imaging system, comprising:
 an image acquisition system;
 at least one marker; and
 a marker detection system.

The X-ray image acquisition system comprises an X-ray source and, opposite said X-ray source across an examination region, an X-ray detector. The X-ray source is configured to emit radiation in form of an X-ray beam detectable at the X-ray detector as a signal after passage of the X-ray beam through the examination region. A volume irradiatable by the beam in the examination region defines a field of view (FoV) of the image acquisition system. Said detector signal is convertible into an image of a sample when said sample is resident in said field of view (FoV) during image acquisition.

The at least one marker is spatially arranged in association with an area, wherein the marker detection system is configured to issue a control signal to the X-ray imaging system in respect of said area when the detection system detects, via at least one of said at least one marker, that i) the area is at least partly within the field of view FoV or ii) the area is within a predefined distance of the FoV. Preferably, the control signal corresponds to the image acquisition instructions encoded in the at least one marker being detected.

The at least one marker is configured to encode one or more image acquisition instructions that correspond to the control signal.

Within the scope of the invention, "encoding" shall be understood to mean possessing information or having one or more properties or a setup, from which image acquisition instructions may be derived through detection of the specific information, properties or setup. For example, distinguishable values of properties like shape, color, degree of absorption or reflectivity may be detected and converted or translated into corresponding instructions. Alternatively or in addition, markers may be provided with certain patterns that correspond to specific instructions. Such pattern may, for example, also comprise a barcode, QR code or the like.

In other words, the at least one marker is provided with one or more specific and distinct features, the detecting of which allows for a specific image acquisition instruction for the imaging system to be derived.

Preferably, the marker(s) form(s) a "mask" for the area. The area may be the area to which the image acquisition instructions relate, for example an area may be indicated that is to receive no or at least less dosage than the surrounding area. Conversely the area may be one that is to receive the radiation and the outside area is not. Markers can be rings, special patches (consumables), drawings, (removable) tattoos and others. Put differently, in one embodiment the marker(s) is an (additional) object(s) and is arranged in respect of the area specifically so as to make the detection of said area more robust.

After the object is recognized or detected, an image acquisition instruction is derived which, in one exemplary embodiment, is a dose reduction action effected by the control signal. In one embodiment the control signal is already issued when the area is approaching the field-of-view but is not yet inside the FoV. This adds a further "security layer" to better protect against unnecessary radiation dose as it gives the user more time to react accordingly.

"Sample" relates herein to the object whose internal structure one wishes to image. The sample may include in particular (but not necessarily) organic or living objects such as a human or animal patient or part thereof.

According to one embodiment, the at least one marker is arranged on a part of the sample and the area is one on the sample. For instance, if the sample if part of a human patient, this marker arrangement allows defining virtual "lead apron" or "lead patient drape" which may be useful when X-raying children in a hospital or GP setting. As is well known, in particular children, when so treated in hospital are subjected to tremendous stress. The situation is aggravated when X-ray imagery is necessary and the child is made to wear clumsy and heavy lead vests to protect body parts from X-ray radiation. The present invention helps relegating the use of such vests to the past. Instead of using vests, to define the area of interest that is to receive the radiation and in the same way to define the area that is to be protected from radiation the one or more markers are simply applied to the child's body. The markers can be chosen as cheerful symbols such as stickers of animals or characters from comic strips or movies. The in general cheerful symbology may help making for a less stressful hospital experience. The markers in the form of stickers, patches or even (temporary) tattoos are applied to define the area that is to be protected from radiation. In one embodiment the marker detection system when detecting the markers will then effect an automatic collimation around the area. The markers may also be applied in forms of drawings, for instance, drawing a loop with special ink, for instance X-ray visible ink to so define the area.

According to one embodiment, the at least one marker is arranged on a body part of a human operator of the X-ray imaging system, the area being one on said body part. According to one embodiment, the body part is a hand of the human operator. This allows combating unwanted radiation of the interventionist hand or other body parts (eg feet) during an interventional procedure.

"Arranging the marker(s) on the patient or human operator" as used herein includes arranging the marker(s) directly on the patient's or human operator's body part (so as to be in contact with the operator's or patient's skin) or may be indirectly arranged for instance, on a wearable item, such as a garment (eg, a medical glove or gown etc), wearable by patient or human operator.

According to one embodiment, the at least marker is configured to encode how and/or which type of an image acquisition action is to be performed. Put differently, in this embodiment the nature of the image acquisition instruction is encoded in the markers. For instance, the markers' shape or their setup can indicate an explicit direction for dose reduction, e.g., which part of the examination region/image is to be collimated. In other words and according to one embodiment, the marker's physical properties and/or their setup can indicate the desired direction of X-ray filtering (that is, which part of the image shall be filtered out or which part is to be retained in the FoV). For instance, in one embodiment, the optical markers include components capable of indicating direction such as an arrow component or the like or the marker itself is shaped like an arrow. In other words, the marker detection system is capable of "reading" out, from one or more specific features of the markers being detected, what to do and how to do it. For instance, the arrow components encoded the "what" (e.g., collimation) and the arrow direction encodes the "how" (protect or reduce radiation in the area pointed at by the one or more arrows. Other encoding schemes by color, degree of absorption, reflectivity, presence of certain patterns etc. are also envisaged and the "arrow" embodiment is an exemplary embodiment only. According to one embodiment, the marker is at least one of i) an X-ray visible, ii) a visual marker, iii) infra-red marker. In other words, the marker detection system runs a feature extraction algorithm that detects the markers and thereby recognizes the area of interest or "area of concern" (e.g., doctor's hands). The markers and feature extraction may be based, without limitation, on any single one or a combination of the following technologies:

X-ray visible markers which recognized be feature extraction on live X-ray images;

Visual markers on the object which are recognized by feature extraction on "optical" images;

IR markers on the object which are recognized by feature extraction on infra-red images.

This list is not exhaustive and other suitable technologies, such as depth sensing is likewise envisaged herein.

According to one embodiment, the marker detection system operates to detect the at least one marker in an X-ray image of the at least a part of the examination region and/or wherein the marker detection system operates to detect the at least one marker (MK) based on non-ionizing radiation reflected from said at least one marker. Using IR or visible light allows operation of the marker detection even without (initial) X-ray exposure.

According to one embodiment, the control signal causes an image acquisition action that facilitates reduction of radiation dosage in said area (A), including at least one of:

i) adjusting a shutter device of the imaging system so that the area is exposed to less radiation than before, ii) (automatically) changing an operation mode of the X-ray source, iii) causing a relative motion between the markers sample and the X-ray source. For instance, as per iii) the sample may be moved relative to the X-ray source by controlling a motorized examination table and/or by moving the C-arm or gantry (holing the X-ray source) relative to the sample or hand. Dosage may be reduced in this manner by moving the area out of the FoV or X-ray beam.

According to one embodiment the control signal causes a suitable transducer issuing a visual or acoustic alert signal either in combination with any one of the previous image acquisition actions i)-iii) or instead of said image acquisition actions i)-iii).

According to one embodiment, the changing of the operation mode comprises reducing an intensity of the X-ray beam achieved in particular by reducing an operating voltage of the X-ray source and/or by reducing a pulse-rate.

The adjusting of the shutter device (eg, collimator) may comprise automatically applying irradiation filters. The distinctive warning signal to the user may for instance be useful in reminding the user to (briefly) step out of the pedal, that is, to take steps to cease irradiation.

Moving the sample relative to the X-ray source may be effected by controlling a motorized examination table (where is sample resides during examination). Suitable collision detection systems are envisaged for this.

According to one embodiment, the control signal determines a motion of at least the X-ray source relative to the sample and/or area. This allows improving workflow. For instance, the position of a marker having a specific color, shape, pattern or the like determines that a rotational acquisition should start/stop at the specified location. Once the corresponding markers are detected, the ACS changes the direction of rotation of the X-ray imaging system.

The detection attempt and/or action initiation is repeated at (possibly adjustable) time intervals (sample rate) throughout the image acquisition or before commencement of the actual image acquisition to effectively track the area. The X-ray imaging system as used herein may be an interventional X-ray imaging system such as of the C-arm or U-arm type. However, this is purely exemplary only as other imaging systems such as CT imaging systems are also envisaged herein.

In one embodiment the marker detection system operates during actual exposure by X-ray radiation, that is, whilst the X-ray source is energized. However, in other embodiments the system may operate prior to actual X-ray dosage exposure. In this "preventive case", if the marker is detected to be inside or within the pre-defined distance of the currently set FoV, the energizing of the X-ray source is blocked and X-ray exposure is allowed to commence only once the marker or all markers or more than a configurable number of markers have been removed from the field of view and/or a suitable preventative image acquisition instruction is carried out, for instance, deployment of collimation blades to block out the area.

One advantage of the proposed system is that, because of the markers, an otherwise complex, computationally expensive and error prone X-ray image based area (such as of hand or other body parts) detection becomes more tractable, robust and reliable.

Another advantage is better and more comfortable patient dosage reduction. For instance, concerning patient protection, the X-ray field of view can be larger than the region of interest during rotational scans (in order to make the rotation feasible). Some "proximity" area might be irradiated without sufficient clinical added value (eg, irradiations of neck in some head scans). The markers allow protecting some patient's specific areas from radiation whilst avoiding the need for patients to wear (lead) shielding vests or aprons that cause intimidation and physical discomfort.

It will be appreciated form the above that the proposed system allows inter alia to help address both, the staff and patient irradiation problem, by using the same underlying principle, namely, markers and their detection.

The "term image acquisition instruction" as used herein relates to parameter settings of the imaging system that determine the imaging geometry actually used or to be used in a given image acquisition.

In summary, the system affords simplifying detection task of areas of concern such as hands with the added benefit of increased detection accuracy by using the dedicated markers in conjunction with the marker detection (sub-)system. The (special or dedicated) markers are applied for area definition so as to make recognition of said area easier at less computational cost, and in a robust way. The markers setup can indicate in an explicit fashion to the marker detection sub-system in which part of the image the filtering must occur (explicit). In other words, the marker-guided detection scheme as proposed herein does not merely rely on un-guided automatic detection of an area of interest/concern (such as the patient body part and/or interventionist's hand or part thereof) in and of itself whose structural "signature" may differ considerably from instant to instant as has been proposed elsewhere. The detection failure rate may be reduced with the proposed marker system as compared to the solution in U.S. Pat. No. 6,435,717 say, whose "motion detector style" system may already issue a warning signal when in fact an object other than that of interest happens to be in the beam. These "false positive" detections may hamper clinical workflow, for instance, by unnecessarily distracting the interventionist.

The same sort of set up might be used to prevent exposing some specific patient's body parts.

According to another aspect there is provided the at least one marker that encodes the image acquisition instructions in a manner and for the purpose as described above.

The marker, according to one embodiment, is included in a wearable item, that is, a garment item wearable by the human operator or the patient to be imaged. The at least one marker is incorporated, arranged on or otherwise applied to the wearable item and the area is defined by said markers when the wearable item is worn. Suitable wearable items are hand or foot wear, such as gloves or (over)shoes. In particular medical gloves (formed for instance from rubber such as latex, or from neoprene, or any other suitable material) as used for interventional or exam procedures are envisaged herein. Because the protection from the radiation derives from the manner in which the markers and marker detection system interact to control the imaging system as described above, more cost-effective, simple, disposable gloves can be used instead of more expensive versions of gloves that include a radiation protective lining (although the use of the marker with such gloves are not excluded herein). The marker may also be laid out or arranged on a shirt, jacket, medical gown or other torso (or leg) garment to define the area on the operator's or patient's arm, should, chest, leg etc.

BRIEF DESCRIPTION OF THE DRAWINGS

Exemplary embodiments of the invention will now be described with reference to the following drawings, it being understood invention may take form in various components and arrangements of components, and in various steps and arrangements of steps. The drawings are only for purposes of illustrating the preferred embodiments and are not to be construed as limiting the invention, in particular are not to scale.

DETAILED DESCRIPTION OF EMBODIMENTS

Figure 1:
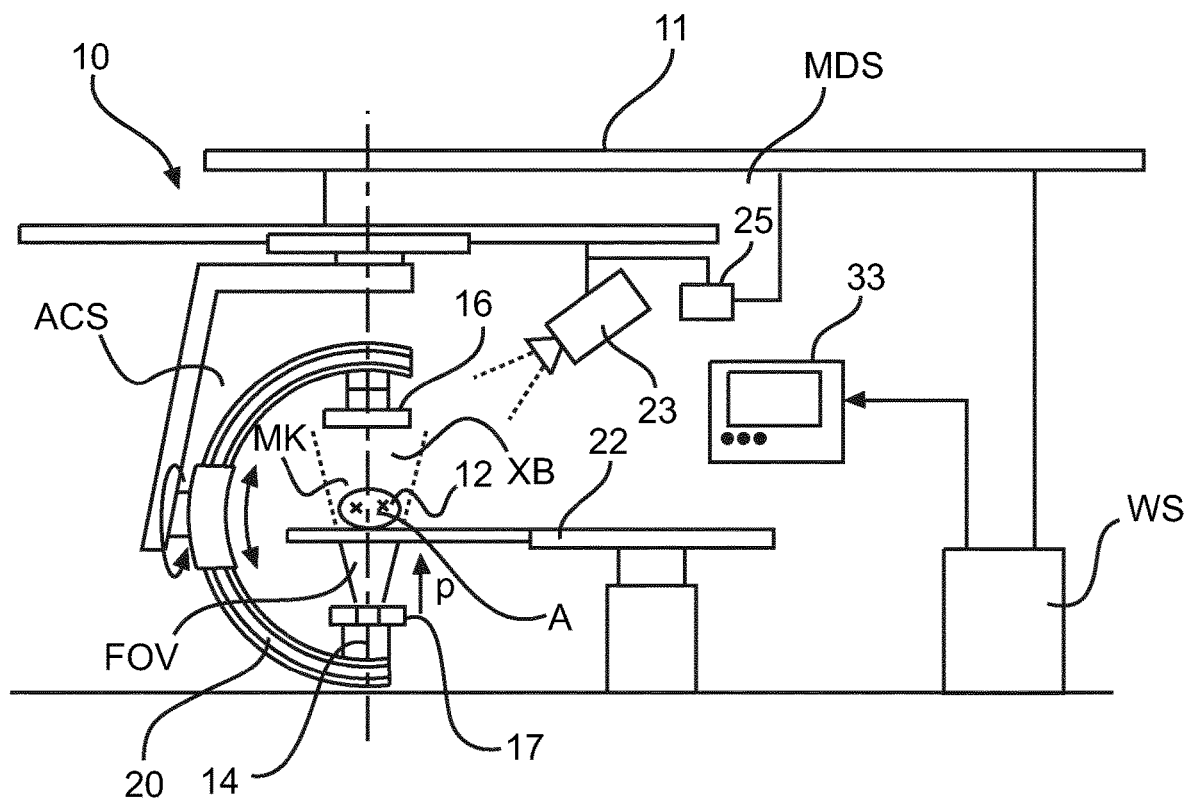
FIG. 1 shows an imaging arrangement according to one embodiment.

With reference to FIG. 1 there is shown an X-ray imaging arrangement 10. The imaging arrangement may be used for example in an interventional procedure by an interventional radiologist (hereinafter "user" or "operator") to provide image based support of the procedure. The imaging arrangement 10 broadly operates to supply one or more images of the internals of a sample 12 (for instance a human or animal patient), which is supported by an examination table 22 in an examination region.

The imaging arrangement 10 broadly includes an image acquisition (sub-) system ACS and a marker detector (sub-) system MDS.

The image acquisition sub system ACS includes in one embodiment a rigid C-arm 20. At one end of the C-arm 20 there is affixed an X-ray detector 16 and at the other end there is affixed X-ray source 14. The arm 20 and with it the X-ray source and/or the detector are arranged to be rotatable around the examination region in which the object 12 resides during an image acquisition. The C-arm 20 is rotatable around one or more axis as shown diagrammatically in FIG. 1 by the curved arrows.

Overall control of the image acquisition is via a computer console or work station WS which is communicatively coupled via a communication means 11, for instance a data bus with the acquisition system ACS. There are also user interface means such as a pedal or push-buttons, or similar, so that the interventionist can request upon pedal or push-button action that the X-ray source is energized to emit radiation whilst the pedal or button is engaged. Joystick controls (or other control means capable of imparting to the user as sense directionality) may also be provided to allow the user to effect moving the C-arm 20 (and with it the source 14) into a desired position/configuration relative to sample 12.

FIG. 1 shows exemplary a ceiling mounted image acquisition sub-system ACS however this is understood to be purely exemplary and not limiting in any way what will be explained further below. In particular, the acquisition system ACS may not be roof mounted but may be floor mounted (on a stand) or may in fact be mobile. Also the communication means or data bus 11 is shown as routed in the ceiling of the examination room and it is understood that this is also purely for exemplary reason as the communication means may also be routed in the floor. Communication may be wireless or wired. Very broadly, during the imaging acquisition one or more images are supplied by the image acquisition system ACS to the work station WS via the communication channel 11. The images may then be viewed on a screen or monitor 33 by the interventionist during the intervention. Monitor 33 is mounted on a suitable stand such an articulated arm (not shown) so that monitor 33 can be moved with ease into a convenient position for view.

One of the basic purpose of the imaging arrangement 10 is to supply images to provide image guided navigation, for instance, to help the user navigate a medical tool inside the patient 12. Examples of such interventions are PCI (Percutaneous Coronary Intervention) where a catheter is introduced into the vasculature of the human heart and needs to be advanced to a lesion, such as a stricture. At times, lots of vascular bifurcations will need to be negotiated to safely arrive at the lesion so reliable imagery is of import. In PCI applications, which are chosen herein purely for illustrative purposes and are not to limit the invention in any way, after administration of a suitable contrast agent, the imaging system 10 operates to acquire not only one but actually a time series or sequence of X-ray images at a suitably defined frame rate as C-arm 20 sweeps out an essentially continuous (up to the applicable, angular step width) arc around the ROI. The image stream is then rendered for view on screen 33 by image processing software running on the work station WS. The interventionist can therefore "see" how the tool is moved through the patient's internal structure.

In order to lay bare the internal structure of the sample 12, use is made of inhomogeneous distribution within sample 12 of radiation absorption coefficient. Other imaging techniques such as phase contrast imaging are also envisaged herein where the distribution of the local refraction index is used instead to form the image(s). Different tissues and structure will absorb the X-ray differently and this can be used to produce an image by suitable DAS (digital acquisition) software running on the workstation WS. The images afford projection views along different projection directions.

The directions are chosen by making the C-arm (and thus the X-ray source) move into different positions relative to the patient (or by moving a suitably motorized examination table relative to the patient 12). Images from different views may also be reconstructed into 3D volumes of a region of interest ROI of patient 12. Again, the present invention is also applicable for indications where only a single, on-off image is required or when merely a few, discretely spaced images are taken and there is no need, eg, for a volume reconstruction.

The X-ray beam XB has in general a cone or a fan shape and defines, within the examination region, a volume that is irradiated during image acquisition by primary radiation. This irradiated volume defines a field of view FoV, in other words anything (with a required density) residing in said volume or FoV whilst the beam "floods" the volume will have their footprint recorded in the projection image (with more or less contrast). Primary radiation is distinguished from scatter radiation in that primary radiation direction is in general from the X-ray source towards the detector as indicted by arrow p in FIG. 1. Arrow p ("projection direction") shows the direction of the center ray of the X-ray beam.

Modern image acquisition systems ACS as shown in FIG. 1 are capable of assuming a multitude of different spatial positions or configurations relative to the sample 12. The image acquisition is either automatic according to an imaging protocol stored on the console or a workstation. The protocol comprises a series of predefined image acquisition instructions or commands. Alternatively, one or more image acquisition instructions are requested ad-hoc as a stream of commands issued by the user from console WS, for instance by setting up tube voltage or by requesting energizing the X-ray source (by operating the pedal say) or operating joystick to move C-arm into a desired configuration relative sample 12, etc. Processing said imaging instructions causes a number of control signals to be issued from the console to the image acquisition system ACS by suitable signal processing components and circuitry. In response to those signals, a signal processing chain of drivers/interfaces and actuators (stepping motors or others) cause for instance the C-arm to move so that at least the X-ray source traces out one or more arcs about the examination region to acquire images from different projection directions p. The different positions of the X-ray source relative to sample 12 and the shape (cross-section) of the volume or beam (extent of FoV) are described herein by the term "imaging geometry". In other words the imaging geometry defines where the X-ray beam's center ray is passing or is to pass through the examination region. Ideally, the sample 12 is so positioned that the region of interest comes to lie within the beam XB that is within the (to be) irradiated volume or FoV. Another parameter which is important to describe and to specify a desired imaging geometry is the width or cross-section of the X-ray beam which can also be changed in one embodiment. In one embodiment, beam cross-section is specified by image acquisition instructions to a shutter device 17 such as a collimator. The shutter device or collimator comprises one or more moveable, in general radiation opaque, metal blades 18 to block out unwanted primary radiation. In this manner the FoV (in particular the cross-section of the radiation beam) is restricted so as to radiate only the ROI in sample 12. In this manner dosage exposure to the patient can be minimized. Another acquisition instruction is the SID (source-to-detector distance) that has a bearing on the FoV and other parameters such as the magnification.

A shutter device 17 is in general arranged in proximity to the X-ray source where the beam egresses the X-ray tube. The shutter device operates to form a shape of the X-ray beam and/or can influence the intensity of the X-ray across a cross-sectional plane of the beam. Shuttering elements such as "wedges" or blades can be positioned within the X-ray beam to locally block-out or at least shade (that is, lessen) radiation intensity received in the examination region. The position of shuttering elements such as "wedges" or blades or others can be controlled by a shutter control device.

In one example, the shutter control device 19 (see FIG. 2) receives the control signal (in response to the image acquisition instruction) in form of a shutter control signal. This signal is translated to control signals for collimator actuators (eg, stepper motors) of said shutter elements to adapt a certain position and thus to effect a certain shape of the X-ray beam.

The shape of the X-ray beam relates to a geometrical shape in a plane or dimension transversely to projection direction p, which can be seen as a virtual connection line between X-ray source and X-ray detector. In other words, the shape relates to a cross-sectional shape of the X-ray beam.

In one embodiment collimator 17 includes, in addition or instead of the X-ray radiation-opaque blades, movable "wedges" (not shown) made from brass sheet or other non-radiation-opaque ("transparent") material that can be slid into the beam or FoV. Said wedges are likewise movable by actuators. Interposing said wedges make part of beam XB impact patient 12 at lesser intensity than the remaining part of beam XB. The respective sheets from which the wedges are formed have a thickness (in direction of the traversing X-ray beam XB) that decreases from its center to its edges. The wedges are essentially filters elements. "Sliding-in" of the wedges allows smoothing the radiation intensity drop around the collimator aperture edge or to change the spectrum of the beam to compensate for beam hardening effects. Finally they can be used to locally reduce the radiation intensity if a complete block-out is undesirable (as would be the case when deploying the blades instead of transparent wedges).

Although in the embodiment of FIG. 1, patient 12 is shown to lie on the examination table 12 during the image acquisition (or "run"), this is not so necessarily true for all embodiments. There are other ACS embodiments envisaged herein where the patient 12 does not necessarily lie flat on the examination table 22 during the examination but where the patient is actually sitting upright or is in fact standing in the examination room (in a designated area, say) between the X-ray detector and the X-ray source with at least the X-ray source possibly rotating around the patient 12 during the acquisition. Also, in mobile imaging solutions, the radiation detector 14 is not physically connected to X-ray source via a gantry 20. In those mobile solutions, there is rather an autonomous (that is, freely movable) detector plate and patient is suitably positioned (lying or standing) between said plate and the X-ray source, with the X-ray source mounted on an articulated arm (or similar) not unlike in dental X-ray imaging system (which are also envisaged herein).

In order to effectively control the image acquisition operation of the ACS, in particular adaptively change the imaging geometry such as the position and/or width or cross-section of the beam, the arrangement 10 as proposed herein further comprises a marker detection (sub-)system MDS. It is envisaged that one or more marker bodies MK (shown as small crosses in FIGS. 1,2) are deposited in the examination region so as to define an area A in respect of the image acquisition. The imaging geometry is then adjusted upon detection by the MDS system of the position of said marker(s) MK in the examination region.

Broadly, the marker detection sub-system MDS 13 comprises in one embodiment one or more cameras 23 and a signal processing module 25 communicatively coupled with said camera 23 and console WS to issue suitable control signals 28 (see FIG. 2) to the same and ultimately to the ACS system. In another embodiment communication of the signal processing module 25 is not via the console WS, as previously explained, but via direct communication with relevant actuator components within the acquisition sub system ACS to adjust, say collimator blades, filters or C-arm position to name just a few actions. According to one embodiment, the control signal issued by the MDS caries into effect an image acquisition instruction. For instance, in one embodiment the ACS responds to the instructions by carrying out an action (such as a collimation operation but this exemplary only) so as to prevent or at least lessen the radiation dosage received at the area A defined or demarked by markers MK. The area A may be a body part of the interventionist, in particular a hand. This is beneficial because interventionists are frequently required to remain close to the patient during the image acquisition and, to make matters worse, would have had their hands exposed to the beam XB during acquisition if it wasn't for the dose reducing operation of the MDS as proposed herein. However the image acquisition instructions effected by the MDS upon marker detection are not restricted to dose reducing actions but other image acquisition instructions are likewise envisaged herein such as table or C-arm movement etc. as will be explained in more detail below.

Figure 2:
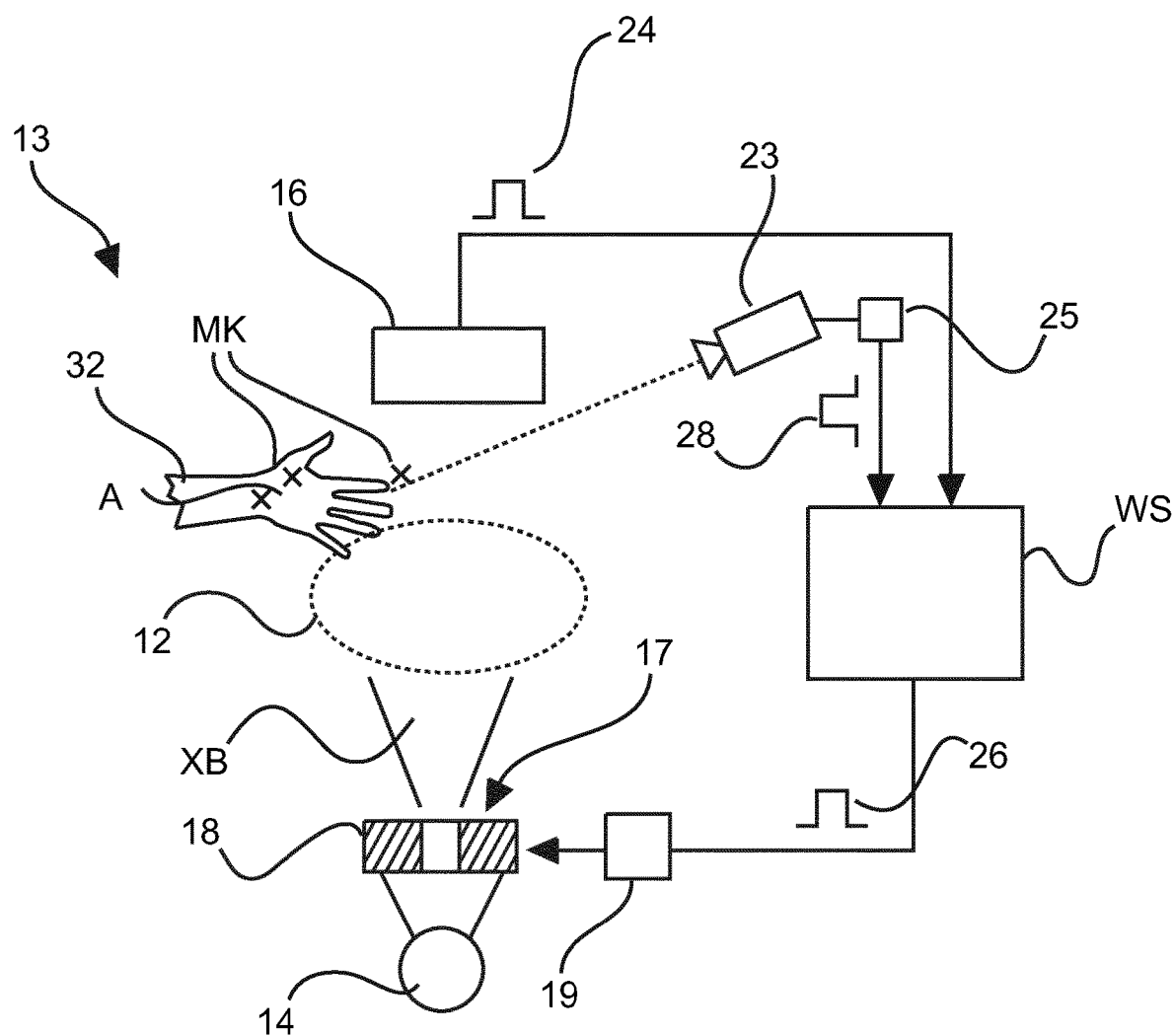
FIG. 2 shows a marker detection sub-system of the imaging system of FIG. 1.

Operation of the marker detection sub-system MDS will now be explained in more detail with reference to FIG. 2. A signal marker MK or a plurality of markers MK are deposited on a body part of the user, for instance on his or her hand, or are deposited on a body part of the patient 12 itself, or are deposited both on patient and user body parts. The one or more cameras 23 then send out non-ionizing radiation, say infra-red or visible light, to capture the current position of the markers and hence that the associated area A within the examination region.

Because the current imaging geometry is known by the system (that is, it is assumed the image acquisition system is "imaging geometry aware") and because the relative position between the cameras 23 and the image acquisition system ACS (in particular the X-ray source and or X-ray detector 17) are likewise known, the reflected non-ionizing radiation received from the markers can be resolved (for instance by triangulation or similar techniques) into spatial information on the relative position between the one or more markers and the current width and/or position of the X-ray beam or the field of view. In other words, processor 25 is capable to reach a decision on whether at least one or more of the markers are indeed within the beam or are less than (in one embodiment) user adjustable distance from the beam, or at least are currently within the field-of-view (or are within the predefined distance thereof) if the actual irradiation has not yet commenced. The marker-beam distance defines a security margin. Said distance may be established by using the position of the marker closest to the imaginary line of the center ray and using the relevant beam width. These quantities can be computed from the current imaging geometry settings.

It should be noted that the embodiment showing a camera component 25 is merely according to one embodiment. In an alternative embodiment there is no extra camera component, but the marker detection system operates instead on the X-ray images themselves as acquired at the X-ray detector 16 of the image acquisition system ACS. Of course a combination of these alternatives is also envisaged herein.

An image acquisition instruction in the form of a signal is issued by the signal processing module 25 to influence the image acquisition in response and dependence on to the marker detection. One such image acquisition instruction may be to achieve dosage reduction on the area defined by the markers (or to at least facilitate said dose reduction). For instance, one such instruction is to prevent, protect or at least lessen the radiation exposure of the area A by driving, via suitable interfaces 19 and/or actuators, the collimator 17 so as to ensure that for instance the operator's hand 32 is outside the beam XB or FoV at substantially all times. Upon receipt of the control signal 28 by work station WS, suitable interface modules resolve said signal into lower level control signals 24 or 26 that are used to drive the image acquisition sub-system accordingly. For instance, a signal 26 may be used to adjust the blade positions in the collimator 17 to so achieve a dose reduction at the user's hand 32 and/or at the marker designated patient area to be protected from radiation. Other image instructions to prevent or lessen dosage may be issued in the form of signal 24 to the X-ray tube 16 to reduce the operation voltage and/or reduce a pulse rate.

However, the image acquisition instructions as envisaged herein are not to be construed as limited to radiation dosage but may also be used to move the C-arm enhanced at least the X-ray tube 16 around the patient. In other words the control signal sent out to the acquisition system in response to the control signal of the marker detection sub-system may be used to energize the motors of the C-arm accordingly. In this manner the arc which is to be traced up during the image acquisition can be controlled. The markers afford a robust and a computation less expensive detection of the area.

Figure 3:
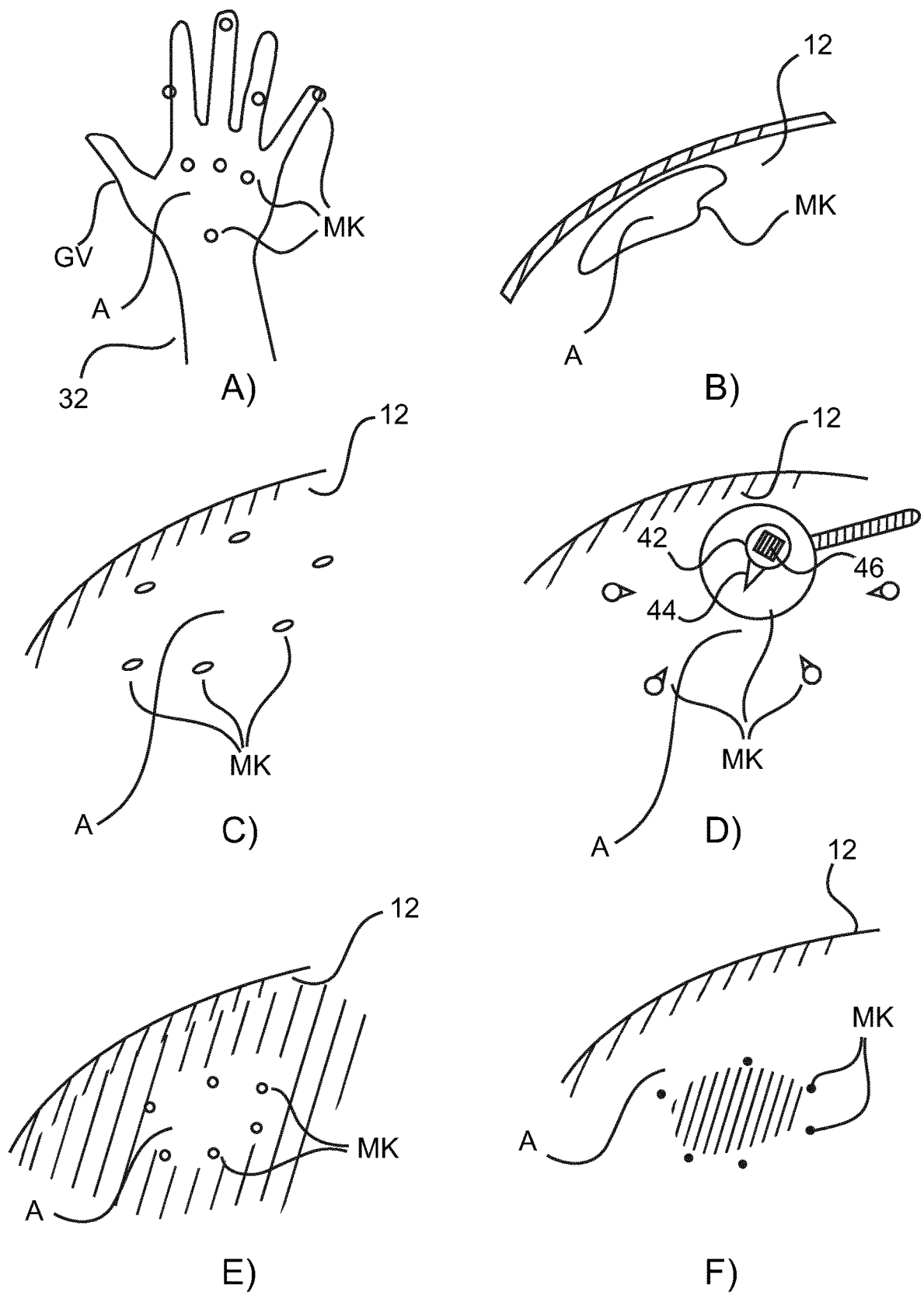
FIG. 3 shows different embodiments of marker arrangements.

The markers themselves are placed prior to the acquisition on the user's hand or are laid out on the patient's body by means of self-adhesive pads (not unlike ECG pads for instance) or are otherwise affixed thereto. In fact, where an ECG is taken, the pads may include special pattern or color-coding to be used for both ECG electrode attachment and for present purposes, for instance, to demark patient chest as an area to be protected or, as inversely, the special ECG markers MK are used to indicate to the system ACS that it is only the chest that is to receive radiation. The markers may be formed from plastic discs or formed from other suitable material. Suitable shapes are spherical or triangular or more complicated shapes as will be explained later with reference to FIG. 3.

The camera component 23 (if any), supplies a respective image of the examination region (where the markers are laid out) formed from the received radiation by operation of the camera sensors. The image type will depend on the technology used so may be an IR image, an optical image. Processor 25 then reads in the image (or different frames if a sequence of images is supplied). Processor 25 operates in one embodiment as a segmenter to segment (that is to feature extract) the image(s) based on the markers' properties (shape, color, etc) depending on the nature of the images supplied. Because the processor is aware of the marker property to be segmented for, a detection with high accuracy can be achieved when compared to approaches where no dedicated markers are used and detection is based solely on say the hand's image footprint which varies from user to user. The markers furnish a stable and precisely defined template so as to guide the segmentation as the segmenter 25 now "knows" precisely what to segment for. Any suitable model-based segmentation technique is envisaged herein where the model parameters are determined by the relevant a-priori known marker properties, that is, its "signature" (color, shape, etc.). The marker-based segmentation is also highly robust against different spatial orientations of the markers as the segmenter 25 knows how the markers look like under different projections. This allows using markers with asymmetries when segmenting for shape although in this case it would appear advantageous to use markers with shapes of high symmetry such as small balls or spheres. The segmentation helps in dealing with objects that are partially visible (e.g.: only 3 out of 5 hand markers are in the X-ray imaging field of view). It should be noted that in the case of plural markers MK, the MDS's segmenter module 25 operates to detect the position of all markers so as to ensure that no part of area A is within the FoV/beam. The performing of the corresponding image acquisition instructions and the respective marker detection may be interleaved however. That is, the corresponding image instruction in respect of a certain individual marker can be carried out right after it has been established that said marker is within the beam/FoV. In this embodiment, the image acquisition instruction for said "rogue" marker MK is executed before the positions of all the remaining markers are established. In other words and for illustrative purposes, when the image acquisition instruction is a collimation, the shutter elements for the individual markers may be observed to slide into place for different markers individually at different instances of time as the segmenter 25 computes the positions of the markers. However that is not to say that said interleaving is used in all embodiments as there may be contexts where all marker positions are established first by MDS segmenter 25 and it is only then that the corresponding image acquisition instructions are carried out.

The detection (feature extraction) itself can be based on any single one or on any combination of the following technologies, such as X-ray imaging, optical imaging, infrared imaging. The non-X-ray technologies here have the advantage that they can detect objects without the need to irradiate, and therefore are expected to result in higher dose savings.

In the embodiment where optical, IR or depth sensing imaging is used, the one or more (eg, optical) cameras can be integrated into the cover of detector 14 (which may be a flat panel detector) or the camera(s) may be integrated in the X-ray source 14 housing.

It is also envisaged in some embodiments to integrate camera(s) 23 into other parts of the system 10 or the cameras may in fact be suitable installed instead in the examination room away from the imaging system 10. For instance, the one or more cameras 23 may be mounted on monitor 33, e.g., at the upper or lower edge thereof or at the sides of the monitor 33.

If the markers have a substantial upwardly extension (that is have "height" so are rather 3D objects than 2D) when applied to or around area A, they then define a relieved surface definition for area A in which case one or more depth sensing camera 23 can be used. Suitable choices for depth sensing camera are Kinect™ by Microsoft of Redmond, Wash., US. The output supplied by such cameras is a depth image which is processed by module 25 largely as described above although in this embodiment module 25 segments for the markers' relief footprint instead of the IR profile (IR visible markers), absorption footprint (X-ray markers) or (relief)pattern/color (visible markers). Similar to the Kinect™ solution, in one embodiment, optical and infra-red detections are combined to reconstruct for a 3-dimensional scene to so determine with great accuracy the marker position relative to the current FoV/beam.

More generally, the different marker detection technologies (and hence the marker types used) mentioned above are either used singly in isolation in certain embodiments, but there are also combo-embodiments envisaged where two or more marker detection technologies are used alongside in combination as the IR+optical in the Kinect equipment. Any combination of the above described marker detection technologies are envisaged herein. To pick out one exemplary embodiment for illustrative purposes only, the marker MKs may be X-ray opaque and be additionally visually (eg, color-coded) encoded. In this case processor 25 detects for the markers MK in two image streams, that is, in one or more X-ray images and in one or more optical images. The positions for the markers from each stream may then be combined to arrive at definitive position for the markers. Other multi-stream examples are depth sensing cameras that provide both, depth images and optical images that are processed by processor 25 in combination.

This redundancy may increase accuracy of the results. The two results may be weighted by a confidence weight such as score which the processor 25 computes for each stream attaching a higher weight to the channel that returned a higher confidence score. Alternatively, in such multi-stream embodiments, it may only be the position with the higher score that is retained and used for a decision on whether the respective marker happens to indeed reside within the current FoV/beam. In this multi-stream embodiment it has been assumed that the very same markers MK are used in both detection procedures. Again, this is true for certain embodiments only, as in alternative embodiments a combination of different marker types are used. For instance, coming back to the "X-ray+optical" embodiment, two types of different markers may be laid out in respect of the area A, X-ray opaque ones and color or patterned ones that are not necessarily X-ray opaque but are transparent. The processor then detects for different markers in the two streams and not as before for different marker properties of the same markers MK.

According to one embodiment the marker detection system MDS operates in tracker mode so as to not only detect the position of the markers but also to track the markers across a sequence of images acquired in a span of time. The geometric check as to whether the marker(s) is within the FoV (or is within the pre-defined distance of the FoV) is then repeated if the imaging geometry changes between two instances of if the marker position changes between two instances.

This tracking operation may be useful when automatically filtering by way of wedges. For instance, MDS instructs filter wedges position to be adjusted with the motion of the markers MK (and hence that of the area A), e.g., filter wedges are repositioned so as to cover the new location of the interventionist's hand or the relevant part of patient 12.

In the embodiment where non-transparent collimation blades are used and detection is based on X-ray imaging, the tracking can be enabled by periodically removing the filter (or applying semi-transparent filter instead). For example, once in a second the shutters are replaced by wedges. This allows combining good tracking capability because the full FoV is repeatedly used with still decent radiation protection because of the relatively short FoV exposure.

FIGS. 3A)-F) show a number of different arrangements of markers according to different embodiments of the invention.

FIG. 3A) shows an arrangement according to a preferred embodiment where a plurality of markers are affixed to interventionist's hand 32. In general, the marker types will depend on the object of interest (eg, human hand), the function of the object in the image (dynamics) and the desired accuracy of the marker and hence area recognition. In other words, the arrangement of the plurality of markers is in a suggestive manner so as to capture not only the geometry of the hand but also is capable of capturing the dynamics of the hand which will enable the detector system to easily detect the position of the markers and hence that of the hand. In "Feature Selection for Grasp Recognition from Optical Markers" (Chang, Lillian Y., et al., IEEE Intelligent Robots and Systems. pp. 2944-2950, 2007) it has been reported that a reduced set of merely five markers allows retain at least 92% of the prediction accuracy of the hands classifier trained on a full set of 30 markers.

The markers are applied to the hand, for instance as per FIG. 3A), or can be built-in into or onto an object cover, eg, a medical glove GV. Simple, disposable gloves GV can be used without radiation protective lining. See for instance "Synergy-based optimal design of hand pose sensing" (Bianchi, M., et al, "Intelligent Robots and Systems (IROS)", IEEE/RSJ International Conference, pp. 3929-3935, 2012) proposing an optimized design of low-cost gloves GV for hand pose processing. The approach there is based on the knowledge of how humans most frequently use their hands in grasping tasks in order to determine how and where to place markers. This approach in Bianchi or similar is envisaged in one embodiment for the manner in which to arrange the makers on the glove GV. In a similar manner, the markers may be arranged in or on suitable foot wear, shirts, jackets, aprons etc or pants to control image acquisitions in respect of other body parts.

The selected marker type is based on the (combination of) detection methods (e.g.: X-ray, optical, infra-red) that is to be used. Their main property is that they are easily detectable by feature extraction. For instance, when X-ray based detection is used it is preferred to use X-ray absorbent materials from markers MK.

Fig. B) shows a "continuous" marker arrangement where the marker is formed as a single object as a band, ribbon or wire formed into the shape of a loop. In contrast to FIG. 3B), the embodiments as per FIGS. 3A),C)-F) may be referred to as "discrete" marker arrangements where a plurality of individual markers are arranged so as to define an area whereas Fig. B) can be thought of as a continuous embodiment where a single marker is laid out as a continuous structure to outline an area. The area itself may be the area inside the markers or the convex hull formed from the plurality of markers.

However in other embodiments it may also be the "complement" of the area with the convex hull formed by the markers that forms the areas one wishes to define. FIG. 3C shows an embodiment where the markers are applied not to the operator's hand but to the patient's body. In FIG. 3C six markers are laid out, for example on the patient's chest or around the neck region, and it is the area circumscribed by those six markers (of course any other number of markers would do) that is to be protected for instance from radiation. Figs. E and F show similar arrangements as in Fig. C where Figs. A, F are complementary or inverse marker arrangements with respect to each other. For instance, in Fig. E the relevant area A in respect of which an image acquisition is to be carried out is the complement of the area circumscribed by the markers. In FIG. 3F however, area A is the inside of the area circumscribed by the markers. More particularly, in FIG. 3F), it is the area inside the markers that are to be protected similar to FIG. 3A. The outside area however is the area of interest that should be imaged so is to receive radiation. The situation is FIG. 3E) is complementary to that in FIG. 3F). In FIG. 3E), it is the outside of the marker circumscribed area one wishes to protect and imaging should be restricted to the area inside the markers. In other words, FIG. 3E) may be used to implement a virtual "leaden patient drape" with the "hole" formed by the area laid out by the markers.

In accordance with the invention, the markers MK are formed to actually encode in themselves image instructions to be carried out in respect of the areas which are defined by the area bordered by said markers. A more detailed view of an embodiment of a marker MK is depicted in FIG. 3D. In particular, one of the markers is shown as a close-up (shown in the schematic "magnifying glass" for illustration). In the shown embodiment, the "smart" markers or image instruction encoding markers comprise a main body 42 and a distinct directional component 44, i.e. a portion encoding a specific direction for an X-ray filtering operation.

The directional component 44 can be shaped as an arrow for instance. In other embodiments it may the whole marker itself that is shaped or arranged as a directional component. The directional component may also be formed as an embossed structure on the main body. In addition or alternatively, the directional component may be applied as drawn/painted on the surface of the main body, eg, in a suitably contrasting pattern or color relative to the background of the main body and or the surroundings in which it is to be used. The directional components embody image acquisition instructions that can be interpreted by the marker detection system MDS by a suitable interpreter component. In this manner it is proposed herein not only to use the markers as geometrical means to detect the area of interest, but also to convey to the system what image acquisition instructions are to be carried out. For instance, if the relevant image acquisition instruction encoded in a marker is one of collimation, the directional components 44 "tells" the system in which direction the relevant area lies in respect of the imaginary line defined by the imaginary periphery traced out by the plurality of markers. For instance, more particularly, in the embodiment of FIG. 3D because the directional components 44 point to the inside of the circumscribed area it is the inside of this area that is to be protected from radiation, in other words this arrangements encodes a collimation instruction (that is a special instance of an image acquisition instruction) where the X-ray beam is to be restricted in the direction indicated by the directional components 44. Instead of or in addition to the directional component 44 the smart marker may also include a specific color, pattern, degree of reflectivity or absorption and/or suggestive symbology 46 in terms of bar codes or alphanumeric symbols or otherwise, which, individually or in combination, encode image acquisition instructions.

For instance, the marker MK may encode by color or pattern a specific voltage to be used by the X-ray tube when performing an image acquisition for an area defined by said smart markers.

In one embodiment the markers may include a set of all image instructions that are to be carried out in respect of the area defined by the markers. The instructions included by the markers may simply be trigger instructions or may be complete instruction sets. In the embodiment where the marker encodes a complete instruction set, the image acquisition system ACS may be instructed directly by the marker detection system MDS. An instruction interpreter component reads in the detected encodings and forms the corresponding control signals. In other words in this case the control signals issued by the marker detection system for controlling the acquisition sub-system ACS may be forwarded merely to an interface unit at the ACS in order to effect translation into lower level commands which then effect the relevant action at the ACS by energizing the relevant actuators or applying the encoded settings, e.g., tube voltage etc. In another embodiment the markers may encode only a simple trigger command/token, that is, the markers do not include a syntactically or semantically complete imaging instruction. In this embodiment the marker detection system MDS merely detects a certain feature through which the encoding is effected. The fact that this feature has been detected is then forwarded as a signal to a work station or other processing unit. The console WS or other processing unit may hold a look-up table that matches each detected feature with the corresponding image acquisition instructions. The matching instruction is then looked-up based on the detected feature, and the image acquisition system ACS is then instructed accordingly by suitable lower level signals.

In summary, in either one of the previous embodiments the actual encoding of the instruction, be it a complete instruction set or a mere trigger token, is by a suitable one or more geometric features/shape(s) of the marker or of a part of the marker or by color- or pattern coding or by any other suggestive symbology printed on the marker. The encoding principle used will depend on the detection technology used. In either of the above embodiments the markers may be fabricated from any suitable material such as plastic, aluminum or any other suitable material that matches the detection technique to be used.

In one embodiment, the directional components 44 encode instruction for the C-arm motion to thereby define start and stop positions of the C-arm motion. The C-arm is so controlled that the FoV remains at all times between the markers, that is, in the area pointed to by the directional components 44 of the markers.

Also in some embodiments, different groups of markers can be laid out to so define a plurality of different areas A. Processing for the different groups is similar to what has been described above. For instance, markers may be used to define the hand area of the interventionist and at the same time other marker groups define areas on the patient's body.

In some embodiments, a marker MK is formed by outlining from the outside or from within the relevant area A with ink or dye such as X-ray visible ink/dye etc or the marker may be applied in form of a removable "tattoo" transferable from paper to skin, not unlike children tattoos sold in toy shops.

In the following, the image acquisition instructions dose reduction purposes as used herein are summarized.

As mentioned above one image acquisition instruction comprises automatically applying irradiation filters to reduce the dose. The filters can be semi-transparent or non-transparent (eg, shutter elements ("blades") of a collimator). At least a part of the FoV is filtered is determined based on the markers properties and/or setup as mentioned above. Using the filter instructions encoded in the markers does not preclude however that in some embodiments other clues are used additionally, such as structural characteristics of the human hand or the relevant patient body part. For instants, knowing the position of some of the markers may already give the MDS a good idea where the remaining markers must be located, because in general terms, the average size of the human hand may be known. In other words, it is not excluded herein that, in some embodiments, certain geometrical constraints of the area defined by the markers are included in the detection computations executed by the MDS processor 25. This filtering is stopped (that is the shutter element is instructed to pull-back to enlarge the FoV) when the markers move out to the previously filtered or blocked portion of the FoV. The image quality in the region of interest is not affected.

Another image acquisition instruction may comprise automatically reducing the dose for the entire image (eg, by lowering pulse-rate or even pause the irradiation). The dose is restored when (all) markers MKs are out of the image. This approach may reduce image quality but still keeps it at sufficient level. Lower demands to image quality can be expected to be sufficient during extraction or insertion of the intervention tools, i.e. when the hands are typically used.

Another instruction may instruct the imaging system to provide a distinctive warning signal to the physician, eg, in form of a visual or audio signal to remind the interventionist to briefly step out of the pedal when using his or her hands. When the non-X-ray based detection technologies are used (optical, IR, depth sensing etc) the warning can be issued when the system ACS is requested to emit radiation from the source and the at least one of the markers MK for the relevant area (hands or patient body part) happens to be inside the current FoV.

As mentioned, any combination of the above summarized image instructions (with or without the warning signal) are likewise envisaged herein, such as automatically filtering and pulse-reduction.

Figure 4:
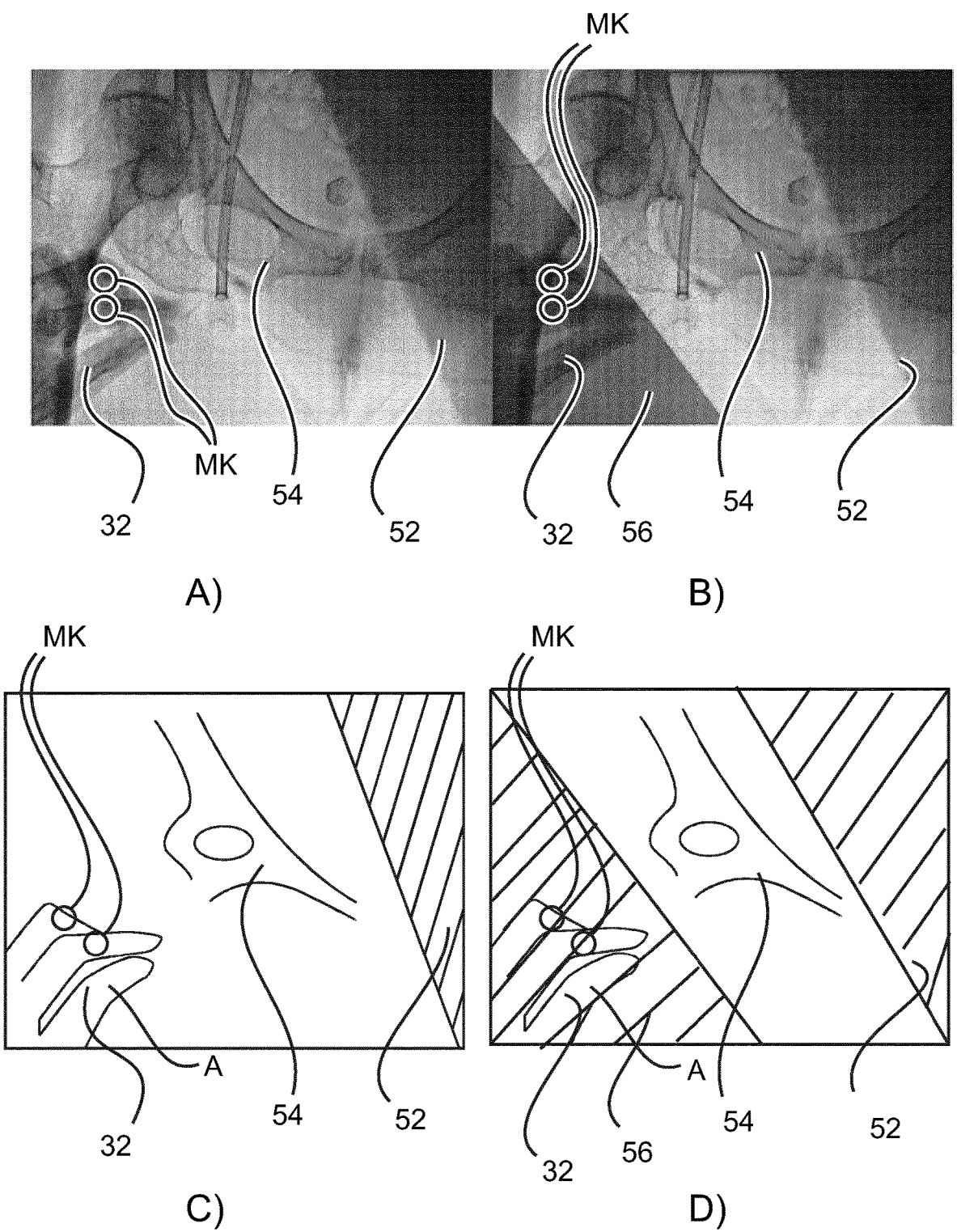
FIG. 4 shows the effect of an image acquisition instruction.

FIG. 4 exemplifies the effect of an image acquisition instruction more particularly of a collimation action.

Figs. A,B show screenshots of two X-ray images where FIG. 4A shows the less desirable situation where the operator's hand 32 is/was within the X-ray beam. Reference numeral 54 indicates a certain anatomic structure of interest and 52 shows the shadow of a deployed collimator or filter element blocking out part of the image or at least reducing the X-ray dosage deposited in that region. FIG. 4B shows the effect after the marker around the operator's hand 32 has been detected. An automatic collimation action occurs where a blade is deployed as to cover the region around the detected marker, that is, the region around the operator's hand, that is, around the detected markers 56. Exactly how broad the collimated part is around the detected markers is determined by internal possibly user definable settings that defines a "block-out margin" around the detected marker positions. This is an example of an image acquisition instruction the purpose of which is to reduce radiation dosage in the area defined by the one or more markers. Reference 56 shows the shadow of the deployed collimator blade which has been slid into position to effect the protection of the physician's hand 32 at the detected marker positions MK. FIGS. 4C,D are schematic renderings of screenshots 4A and B.

Operation of the marker detection subsystem MDS is either alongside execution of a protocol or alongside the user controlling the imaging system. Once the marker detection subsystem MDS detects the marker(s) MK are within the FoV or sufficiently near, the above described actions are carried out automatically, possibly in addition to the user requested control signals or the system overrides a user requested action to enforce for instance exposure protection of the hand 32. For instance, whilst the user operates the joystick to move the C-arm 20, the detection system MDS automatically performs, if required, the necessary collimation action to block out or filter the area A around the user's (or another user's) hand whilst the C-arm moves into the new position.

Figure 5:
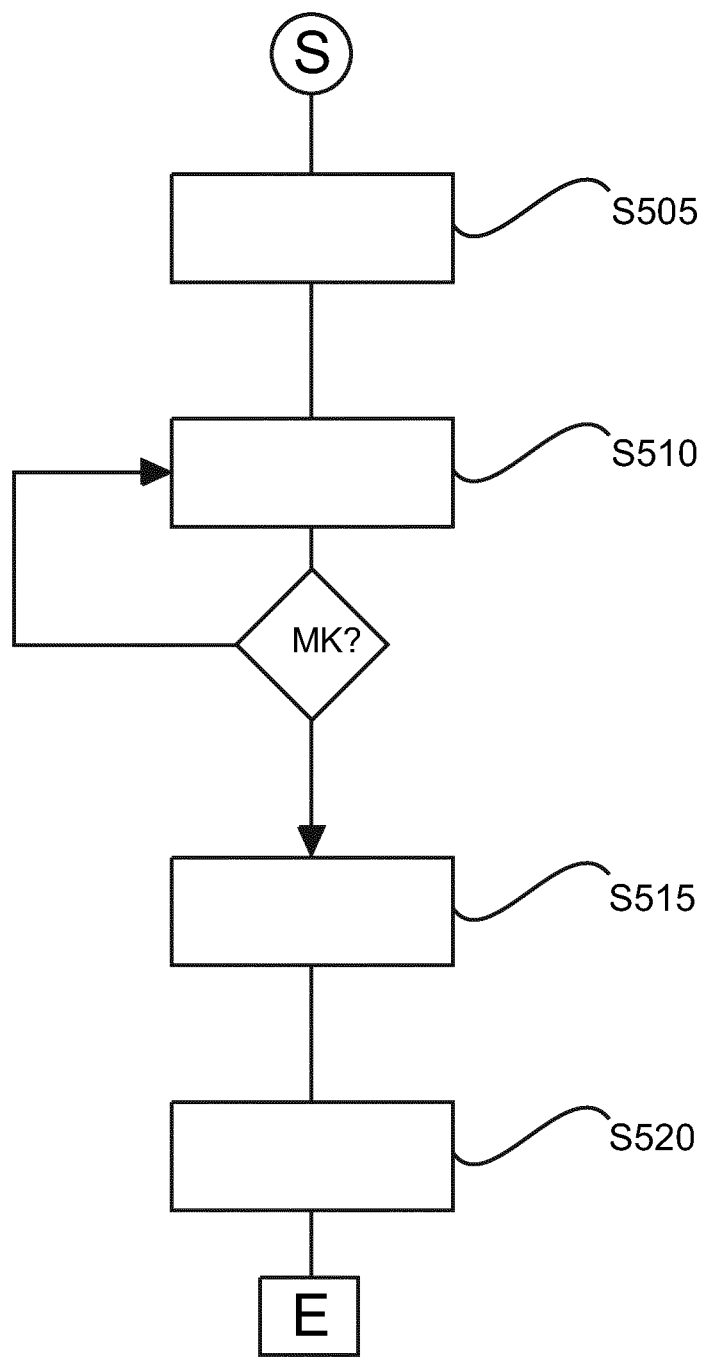
FIG. 5 shows a flow chart of a method of operating an imaging X-ray system.

With reference to FIG. 5 there is shown a flow chart of a method of operating X-ray image acquisition system. The system is suitable to acquire one or more images of a sample, in particular an organic sample, yet more particularly a human or an animal patient (part). X-ray radiation is emitted from an X-ray source and forms an X-ray beam. The beam is detectable at an X-ray detector of the system. The signal detected at the detector can then be translated into the image of the sample when the sample is resident in the examination region formed by the space between the two opposing components, the X-ray source and the X-ray detector.

In a preliminary step S505, one or more markers MK are laid out either on the sample or on a body part of the imager operating user.

At step 510 an attempt is made to detect whether the area is at least partly within the X-ray beam. Alternatively, or in addition thereto an attempt is made to detect whether the area is within a pre-defined distance of the X-ray beam. The area of interest is defined by the laid out markers in spatial association therewith.

At step 515 if at least one of the markers is so detected, an associated control signal is issued to the image acquisition system.

At step 520 the control signal is received and in response thereto an associated image acquisition action is carried out by the image acquisition system in respect of said marker demarked area. According to one embodiment flow control then returns to detection attempting step 510. By this back-looping a monitoring or tracking functionality is implemented.

Detection step S510 may be carried out before X-ray tube is energized as the (to be) irradiated volume/ultimate FoV is already known to the system from current imaging geometry (setting parameter) to be used for the upcoming image acquisition.

In one embodiment it is envisaged to maintain the instruction in operation or in effect for as long as the marker(s)/area so demarked is within the FoV (or is within the predefined distance of same) and to then reverse or disable the instruction once it is detected that the marker is outside FoV or is outside the predefined distance.

Although the above has been explained largely in medical terms, the proposed method and system may also be put to good used in other X-ray imaging contexts such as baggage or passenger screening, or non-destructive material testing and others.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system, comprising:
an image acquisition system;
at least one marker; and
a marker detection system,
wherein the X-ray image acquisition system comprises an
X-ray source and, opposite said X-ray source across an examination region, an X-ray detector, the X-ray source configured to emit radiation in form of an X-ray beam detectable at the X-ray detector as a signal after passage of the X-ray beam through the examination region, wherein a field of view of the image acquisition system is defined by a volume irradiatable by the X-ray beam, with said signal convertible into an image of a sample when said sample is resident in said field of view during image acquisition,
wherein the at least one marker is spatially arranged in association with an area and has at least two features configured to encode one or more image acquisition instructions, the at least two features including a marker feature for detecting a position of the at least one marker,
wherein the marker detection system is configured to issue a control signal to the X-ray imaging system in respect of said area when the detection system detects at least one of said at least one marker and thereby that
i) the area is at least partly within the field of view or
ii) the area is within a predefined distance of the field of view,
wherein the control signal corresponds to the one or more image acquisition instructions for the detected at least one of said at least one marker.

2. The system of claim 1, wherein the at least one marker is arranged on a part of the sample and the area is on the sample.

3. The system of claim 1, wherein the at least one marker is arranged on a body part of a human operator of the X-ray imaging system, the area being on said body part.

4. The system of claim 3, wherein the body part is a hand of the human operator.

5. The system of claim 1, wherein the at least one marker is configured to encode how and/or which type of an image acquisition action is to be performed.

6. The system of claim 5, wherein the at least one marker is at least one of i) X-ray visible, ii) a visual marker, and iii) an infra-red marker.

7. The system of claim 6, wherein the marker detection system operates to detect the at least one marker in an X-ray image of at least a part of the examination region and/or wherein the marker detection system operates to detect the at least one marker based on non-ionizing radiation reflected from said at least one marker.

8. The system of claim 1, wherein the control signal causes an image acquisition action that facilitates reduction of radiation dosage in said area, including at least one of:
i) adjusting a shutter device of the imaging system so that the area is exposed to less radiation than before,
ii) changing an operation mode of the X-ray source, and
iii) causing a relative motion between the at least one marker and the X-ray source.

9. The system of claim 8, wherein the changing of the operation mode comprises reducing an intensity of the X-ray beam achieved by reducing an operating voltage of the X-ray source and/or by reducing a pulse-rate.

10. The system of claim 1, the control signal determines a motion of at least the X-ray source relative to the sample and/or area.

11. A method of operating an X-ray imaging system suitable to acquire an image of a sample by emitting radiation from an X-ray source in form of an X-ray beam detectable at the X-ray detector, wherein a field of view of the image acquisition system is defined by a volume irradiatable by the beam, the method comprising acts of:

arranging at least one marker spatially in association with an area, the at least one marker having at least two features configured so as to encode one or more image acquisition instructions, the at least two features including a marker feature for detecting a position of the at least one marker;

using the at least one marker, detecting whether the area is at least partly within the field of view or at least detecting whether said area is within a predefined distance of the field of view; and when the at least one marker is so detected, issuing a control signal to the X-ray imaging system in respect of said area, the control signal corresponding to the image acquisition instructions encoded in the detected at least one marker.

12. The method of claim 11, wherein the at least one marker is arranged on a body part of a human operator of the X-ray imaging system, the area being on said body part.

13. A non-transitory computer readable medium comprising computer instructions which, when executed by a processor; configure the processor to perform a method of operating an X-ray imaging system suitable to acquire an image of a sample by emitting radiation from an X-ray source in form of an X-ray beam detectable at the X-ray detector, wherein a field of view of the image acquisition system is defined by a volume irradiatable by the beam, the method comprising the acts of:

arranging at least one marker spatially in association with an area, the at least one marker having at least two features configured so as to encode one or more image acquisition instructions, the at least two features including a marker feature for detecting a position of the at least one marker;

using the at least one marker, detecting whether the area is at least partly within the field of view or at least detecting whether said area is within a predefined distance of the field of view; and when the at least one marker is so detected, issuing a control signal to the X-ray imaging system in respect of said area, the control signal corresponding to the image acquisition instructions encoded in the detected at least one marker.

14. The system of claim 1, wherein, in response to the one or more image acquisition instructions, the control signal controls a shutter to shape the X-ray beam.

15. The system of claim 1, wherein, in response to the one or more image acquisition instructions, the control signal controls a collimator to reduce the radiation of an area to be protected from the radiation.

16. The system of claim 1, wherein, in response to the one or more image acquisition instructions, the control signal controls the X-ray source to change the radiation including by changing at least one of an operation voltage and a pulse rate of the X-ray source.

17. The system of claim 1, wherein the image acquisition system is configured to execute the one or more image acquisition instructions after all of the at least one marker is detected by the marker detection system.

18. The system of claim 1, wherein the image acquisition system is configured to execute the one or more image acquisition instructions after the at least one marker is detected by the marker detection system.

19. The method of claim 11 wherein, in response to the one or more image acquisition instructions, the control signal controls at least one of:
the X-ray source to change the radiation including by changing at least one of an operation voltage and a pulse rate of the X-ray source,
a shutter to shape the X-ray beam, and
a collimator to reduce the radiation of an area to be protected from the radiation.

20. The method of claim 11, further comprising an act of executing the image acquisition instructions by the X-ray imaging system after all of the at least one marker is detected.

* * * * *